(12) United States Patent
Tanriverdi

(10) Patent No.: US 9,030,667 B2
(45) Date of Patent: May 12, 2015

(54) SYSTEM AND METHOD TO MEASURE 3D FLOW CHARACTERISTICS OF A GAS

(71) Applicant: General Electric Company, Schenectady, NY (US)

(72) Inventor: Olgu Tanriverdi, Greenville, SC (US)

(73) Assignee: General Electric Company, Schenectady, NY (US)

( * ) Notice: Subject to any disclaimer, the term of this patent is extended or adjusted under 35 U.S.C. 154(b) by 126 days.

(21) Appl. No.: 13/843,442

(22) Filed: Mar. 15, 2013

(65) Prior Publication Data

US 2014/0268158 A1  Sep. 18, 2014

(51) Int. Cl.
*G01N 21/00* (2006.01)
*G01N 21/47* (2006.01)
*G01N 21/53* (2006.01)
*G01P 5/00* (2006.01)
*G01P 5/26* (2006.01)

(52) U.S. Cl.
CPC ............ *G01N 21/4795* (2013.01); *G01N 21/53* (2013.01); *G01P 5/001* (2013.01); *G01P 5/26* (2013.01)

(58) Field of Classification Search
CPC .............. G01N 27/26; G01N 27/4148; G01N 33/54373; G01N 33/6818; G01N 1/22; G01N 1/28; G01N 1/32; G01N 2021/335; G01N 21/00; G01N 21/05; G01N 21/33; G01N 21/3504; G01N 21/39; G01N 21/718; G01N 21/08
See application file for complete search history.

(56) References Cited

U.S. PATENT DOCUMENTS

| | | |
|---|---|---|
| 3,547,540 A | 12/1970 | Shigemoto |
| 3,675,029 A | 7/1972 | Iten et al. |
| 3,858,203 A | 12/1974 | Constant |
| 3,860,342 A | 1/1975 | Orloff et al. |
| 4,167,736 A | 9/1979 | Tomlinson |
| 4,263,002 A | 4/1981 | Sathyakumar |
| 4,396,943 A | 8/1983 | Lord et al. |
| 4,572,664 A | 2/1986 | Hanson |
| 5,563,929 A | 10/1996 | Connolly et al. |
| 5,701,172 A | 12/1997 | Azzazy |
| 6,271,522 B1 * | 8/2001 | Lindermeir et al. ....... 250/341.1 |
| 6,315,955 B1 | 11/2001 | Klein |
| 7,560,869 B2 * | 7/2009 | Miles et al. ............. 315/111.21 |
| 7,728,295 B2 | 6/2010 | Miles et al. |
| 2004/0057650 A1 * | 3/2004 | Folestad .......................... 385/14 |
| 2006/0176486 A1 * | 8/2006 | Ho ................................ 356/436 |

OTHER PUBLICATIONS

"Tunable Diode Laser (TDL) Gas Sensors", TDL Gas Turbine Sensors, www.psicorp.com, printed Aug. 30, 2012, three pages.
Marco E. Leon, "Diode Laser Measurement of H2O, CO2, and Temperature in Gas Turbine Exhaust Through the Application of Wavelength Modulation Spectroscopy", Master of Science in Engineering Sciences (Mechanical Engineering), 2007, 91 pages.

* cited by examiner

*Primary Examiner* — Michael P Stafira
(74) *Attorney, Agent, or Firm* — Nixon & Vanderhye P.C.

(57) ABSTRACT

A method to collect 3D measurement data regarding a working fluid in a system, e.g., a turbo-machine, including: arranging sources of beams proximate to a passage of the working fluid in or downstream of the turbo-machine such that beams from the sources are projected through the working fluid; detecting intensities of the beams after they pass through the working fluid, and generating at least a two dimensional (2D) representation of the working fluid based on the detected intensities of the beams.

16 Claims, 2 Drawing Sheets

SYSTEM AND METHOD TO MEASURE 3D FLOW CHARACTERISTICS OF A GAS

BACKGROUND OF THE INVENTION

The present invention relates to three dimensional (3D) directional velocity measurements of gases flowing through a passage of a system such as at an inlet or exhaust of a gas turbine via arrays of laser beams and detectors set up in two parallel planes with a distance. A method and the set up of arrays of laser beams and detectors are also presented. 3D measurements are important in improving performance, diagnostics, and modeling of the system.

Turbo-machine systems include a rotary component that is driven by a working fluid, such as a gas. For example, gas turbine engines generate power by compressing atmospheric air, adding fuel to the compressed air, combusting the mixture of fuel and air, and driving a turbine with the mixture of combusted gases. The working fluid continuously passes through the compressor, combustor and turbine, and is discharged as it passes turbine.

The working fluid flowing through a gas turbine engine holds information about the operation and performance of the engine. The velocity and direction of the working fluid, the temperature and distribution of temperatures in the working fluid, and the chemical composition of the working fluid reflect the condition and performance of the engine. For example, the exhaust gas provides information regarding the combustion temperature in the combustor, the performance and efficiencies of gas turbine, the constituents of the combusted gases flowing through turbine, and other performance parameters of the system. The 3D characteristic of velocity, flow directions, temperature and components of the working fluid across and cross-section of the flow passage of the working fluid and over time can be particularly telling of the condition and performance of the engine. 3D characteristic of fluid may also be used improving the mathematical modeling of the overall system, e.g., gas turbine.

The characteristics of working fluid are difficult to measure due to the extreme temperatures, pressures and other flow conditions in a gas turbine engine. Temperatures of the exhaust gases from a typical industrial gas turbine engine may be, for example, 900 to 1200 degrees Fahrenheit (° F.) (482 to 649 degrees Celsius ° C.). The mass flow of the exhaust gases may be, for example, 300 to 975 pounds per second (lb/sec) (136 to 442 kg/sec). Swirl in the exhaust creates difficulties in measuring and analyzing the working fluid. Conventional temperature probes, such as thermocouples, and arrays of probes have not been capable of measuring the temperature distribution of exhaust gases over an extended period of operation of the gas turbine engine.

The conditions of the working fluid at the turbine exit and in the exhaust are conventionally not directly measured but are calculated. The calculated conditions are used to control a gas turbine engine. The calculations of the conditions of the working fluid are generally based on engine parameters such as power output, pressure ratio of the compressor, fuel flow to the combustor and ambient conditions. The calculations of the working fluid are based on assumptions and approximations that may not accurately model the actual flow conditions.

The conventional calculations of the conditions of the working fluid do not provide detailed information regarding actual operating conditions in specific locations in the engine, such as a poorly performing combustion can, or instantaneous conditions of the working fluid. Further, the calculations do not provide information regarding distribution of the flows passing through a turbo-machine, such in the exhaust of a gas turbine engine. There is a long felt need to directly measure the flow of a working fluid in or from a turbo-machine in two-dimensions (2D) or in three dimensions (3D) to provide 2D and 3D maps showing the flow and particularly the distribution of the flow in cross-section and over time.

BRIEF DESCRIPTION OF THE INVENTION

A method has been conceived to collect data regarding velocity and flow direction of a working fluid in a system, e.g., a turbo-machine, including: arranging a set of calibrated laser beams and detectors in a plane proximate and perpendicular to a passage of the working fluid in or downstream of the system such that laser beams from the sources are projected through the working fluid; detecting intensities of the laser beams via detectors after they pass through the working fluid, and generating at least a 2D representation of the working fluid based on the detected intensities of the beams.

A method has been conceived to collect and present data regarding velocity and flow direction of a working fluid in a system, e.g., gas turbine or other turbo-machine, comprising: arranging calibrated laser beam sources and detectors proximate to a passage of a working fluid in or downstream of the system such that laser beams from the sources are projected through the working fluid, wherein the laser beam sources are arranged such that the paths of the laser beams and detectors are distributed in a cross-sectional area of the working fluid and each laser beam and detector path intersects with at least one other of the paths and laser beams and detectors align in the same plane; detecting intensities of the beams after passing through the working gas; determining each data value corresponding to the intersection of the paths, wherein the data value is determined by the detected intensities of the beams along the intersecting, and generating at least a 2D representation of the working gas based on the data values. The frequency, intensity, and calibration of the laser beams and detectors may be tuned to achieve desired flow measurements taken of the working fluid.

An apparatus has been conceived to analyze a working fluid passing through a system, e.g., turbo-machine, comprising: a first array of laser sources and detectors arranged in a plane extending through the working fluid as the fluid passes through or downstream of the system; a second array of laser sources and detectors arranged in a plane extending through the working fluid as the fluid passes through or downstream of the system, wherein the second array plane is parallel to and offset from the first array plane along a rotational axis of the system; a controller receiving laser intensity data from the detectors and including a non-transitory memory storing instructions and a processor which executes the instructions to cause the controller to generate at least a two-dimensional representation of at least a cross-section of the working fluid.

A method and system have been conceived to measure gas flow, e.g., a working fluid, entering, moving through or exhausting from a flow passage of a system such as a gas turbine engine, steam turbine or other turbo-machine. The measurements, such as measurements of voltage levels of detectors for each corresponding laser beams, provide information regarding the distribution of the working fluid of the conditions, e.g., velocity, flow direction, temperature and composition. The measurements may be made across the fluid flow in one or more successive cross-section(s) of the flow passage. The information may be presented as 3D data and 3D images.

Laser beams are projected through the working fluid. The fluid flow adsorbs, reflects or otherwise disrupts the beams.

The intensity of each beam holds information regarding the fluid through which the beam passes through. For example, the temperature, composition, e.g., presence of nitrous oxides, and turbulence of the gas flow affect a laser beam and the intensity of the beam at a detector. The intensity of each beam is measured after passing through the flow. The beam intensity measurements indicate the condition of the gas flow along the beam path.

Arrays of lasers arranged around the path of the working fluid pass laser beams through the gas flow and arrays of detectors sense the intensity of the beams. Each array may be in a plane that crosses through the flow path, such as a plane perpendicular to the axis of the flow passage. The lasers may be arranged at various positions around the periphery of the gas flow, such as arranged in a symmetrical array, e.g., rows and columns, about the gas flow path. The number of laser beams and detectors can be increased or decreased depending on the desired resolution of the measurements.

Beam intensity data are obtained by the laser detectors in the array. The beam intensity data are used to generate a three-dimensional (3D) representations, e.g., images or spread sheets, of the gas flow as it passes through the plane.

Three dimensional representations may be generated by arranging the lasers and detectors in multiple planar arrays. Each planar array may be separated by a short distance, such as a few millimeters or centimeters (1 mm to 30 mm). The arrangement of lasers and detectors may be the same in each measurement plane to enhance the comparability of the gas flow data collected in each plane. By combining the data collected in each plane, three-dimensional (3D) images or data presentations of 3D velocity and direction of the flow passing through the measurement planes is generated.

DETAILED DESCRIPTION OF THE INVENTION

Figure 1:
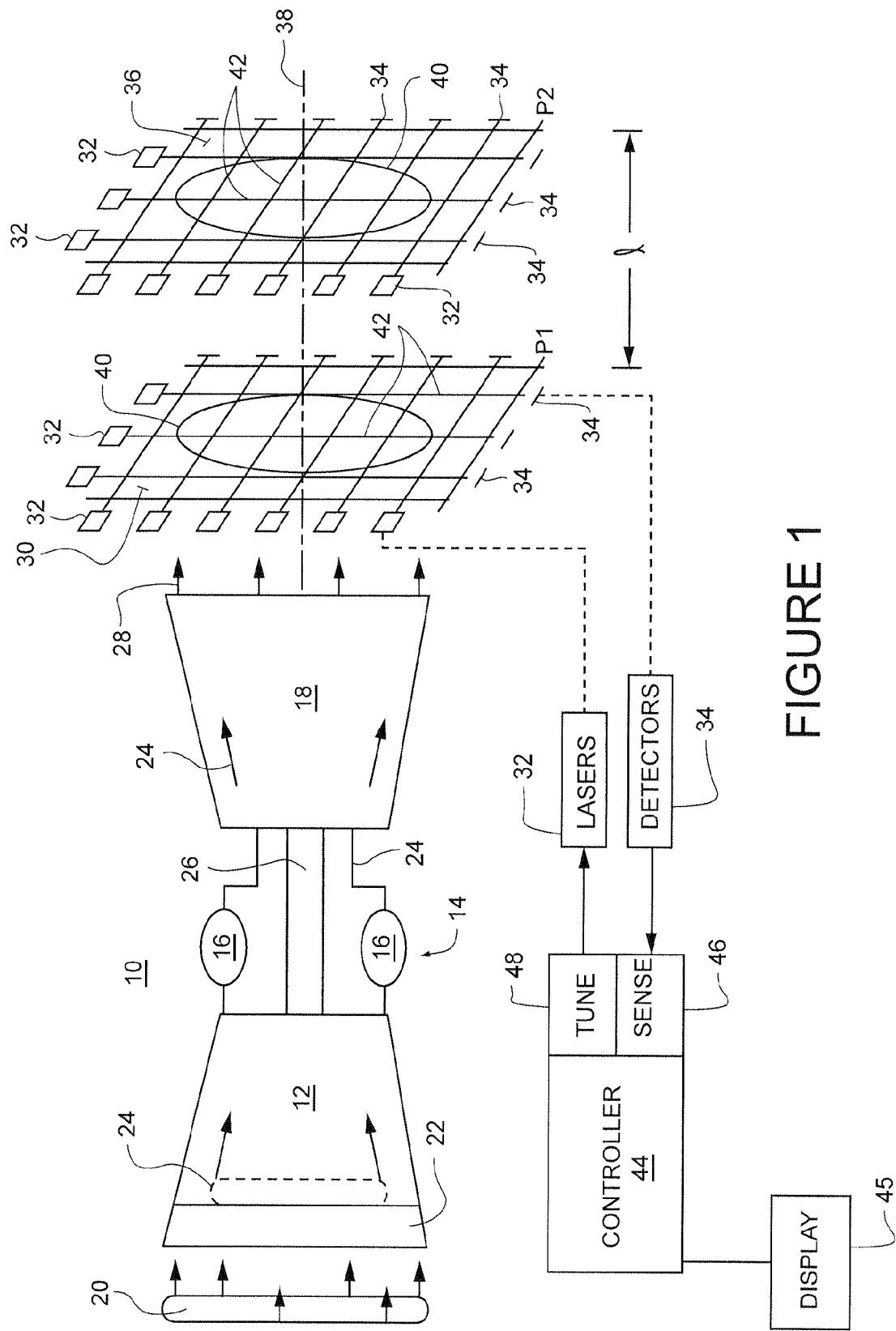
FIG. 1 schematic diagram of gas turbine engine with arrays of lasers and detectors arranged in planes and positioned at the exhaust of the gas turbine.

FIG. 1 is a schematic diagram of an industrial gas turbine engine 10 having a compressor 12, a combustor 14 including an annular array of combustion cans 16 and a turbine 18. A working fluid 20, such as atmospheric air, pass through the inlet guide vanes (IGV) 22 and enters the compressor. An annular gas passage 24 extends through the IGV, compressor, combustor, and turbine. As the working fluid moves through the gas passage, the fluid is compressed in the compressor, is mixed with fuel and combusts in the cans of the combustor, and drives the turbine to produce work typically output by a rotating shaft 26 coupled to the turbine. The working fluid exits the gas passage 24 from the turbine as an exhaust gas 28.

The characteristics of working fluid may be measured by arrays of lasers 32 and detectors 34 positioned in planes along the gas passage or at the exhaust of gas turbine. FIG. 1 shows a first planar array 30 of lasers 32 and detectors 34 and a second planar array 36 of lasers and detectors. Each laser has a corresponding detector. The laser is positioned on one side of the gas passage or exhaust gas and the detector on the opposite site. Each laser emits a laser beam through the gas passage or exhaust gas that is detected by the corresponding detector. For each array 30, 36, the laser and detectors may be arranged in a row and a column around the periphery 40 of the working fluid.

The arrays 30 and 36 are in planes (P1 and P2) perpendicular to an axis 38 of the gas turbine engine. Measurement difference between planes P1 and P2 which contain array of laser beams and detectors provides a 3D representation of the change of flow profile between two planes. For example, beams extending horizontally through the exhaust gases may be separated by a short axial (l) distance, e.g., 0.1 to 0.7 mm to measure the 3D flow change between two planes.

The planes P1 and P2 are separated by a distance (l) in the direction of the axis 38. The distance (l) between the arrays may be relatively short, such as a few millimeters or centimeters, e.g., 1 mm to 30 mm. The lasers and detectors in each array may be arranged at the periphery 40 of a stream including all or most of the exhaust gas or at the periphery of the annular passage. The distance (l) may be selected based on the expected amount of swirl and turbulence in the exhaust gas. The amount of swirl or turbulence in the exhaust gas may be measured by comparing the data collected from the laser beams at each of the planes P1 and P2.

The positioning of the arrays in the planes P1 and P2 . . . Pn may be selected based on the conditions of the gas turbine engine to be sensed, the access available to the gas passage or exhaust gases and the ability of the lasers and detectors to withstand the harsh environment of combustion gases. Similarly, the arrangement of lasers and detectors may be selected based on the portion of the gas passage or exhaust gases to be traversed with the laser beams, the access to the gas passage or exhaust gases, and the information desired to be collected about the working fluid.

Each laser 32 projects a laser beam 42 through the working fluid in the exhaust 28 or gas passage 24. The laser controller 48 may apply a voltage to each of the lasers and collect data regarding the amount of voltage applied to each laser. The laser controller may tune the lasers to a laser beam frequency or level that is selected as being most useful to analyze the working fluid, such as a frequency that is adsorbed by certain emissions in the exhaust gas.

After passing through the working fluid, the beams are detected by the detectors 34. The sensor 36 for the detectors may sense and collect data regarding the intensity of the laser beams received at each of the detectors. The intensity of each beam indicates the extent to which the beam was adsorbed or deflected by the working fluid. The received intensity may be compared to data regarding the voltage applied to the laser to calculate the reduction in intensity of the laser beam due to the passage of the beam through the working fluid. The reduction in intensity of a laser beam passing through the working fluid provides information, e.g., data, regarding the condition of the working fluid, such as the fluid velocity and direction of fluid movement.

The lasers of each array may transmit sequentially to ensure that laser light from one beam is not inadvertently sensed by a detector associated with another beam. For example, the lasers of an array may each emit brief pulses of laser light in a fast sequence, such as a sequence in which all lasers in the array emit within a few milliseconds. Alternatively, all lasers in the array may emit laser light beams as the same time.

Information, e.g., data, from the lasers and detectors are sent to a controller 44, which may include a computer or processor, non-transitory electronic memory such as rewritable random access memory (RAM), read-only memory (ROM) and disc memory, voltage measurement sensors 46 and laser controllers 48, such as voltage controller or a laser frequency tuning controller. The dotted lines in FIG. 1 indicate that the lasers and detectors shown communicating with the controller are the same lasers and detectors in the arrays.

The information collected from the lasers and detectors may be analyzed for information regarding the working fluid in the gas passage or exhaust gas. In particular, the analysis of the information may present at least a 2D representation of the working fluid. For example, the data collected in each plane may be processed using conventional tomography techniques to create at least a 2D image of a cross-section of the working fluid at the plane corresponding to the period, e.g., instant, the laser beams passed through the working fluid. The at least 2D images from successive planes P1 and P2 can be combined to form a at least a 2D image of the profile change of the working fluid, provided that the data was collected substantially simultaneously from each plane.

Figure 2:
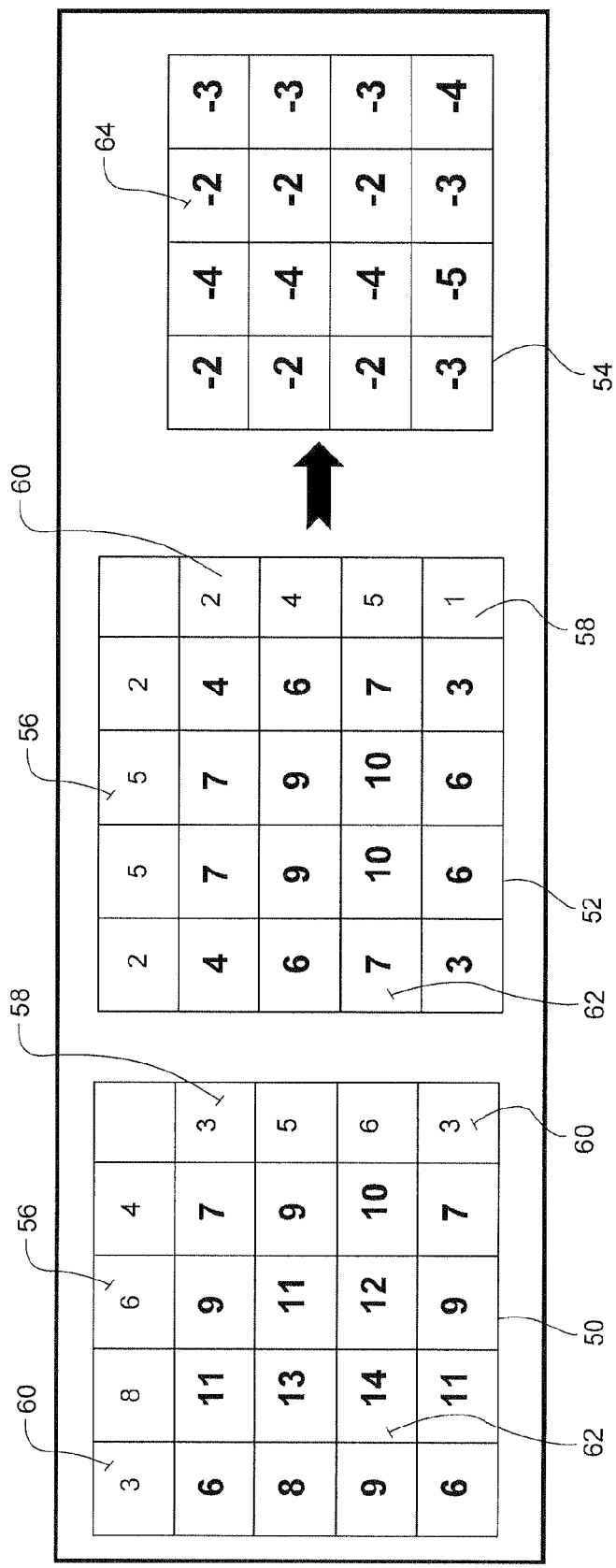
FIG. 2 illustrates two exemplary sets of data collected at each of the planes at exhaust of gas turbine, a third set of data showing the differences between the first two sets of data, thus providing a 3D representation of the change of flow profile between two planes.

FIG. 2 illustrates two exemplary sets 50 and 52 of data collected at each of the planes P1 and P2 in exhaust gas, a third set 54 of data showing the differences between the first two sets of data. Data set 50 represents data collected from the working fluid in plane P1 at an instant from the lasers and sensors in the first assembly 30.

The raw data 60 from the detectors (sensors) are shown in the upper row 56 and last column 58 of the data set 50. The raw data 60 may represent the intensity of the laser beam when it reaches the detector and after having passed through the working fluid. The intensity of the beam is indicative of the extent to which the working fluid adsorbed, reflected or otherwise deflected the beam along the path of the beam and before the beam reached the detector. The intensity of the beam at the detector is representative of the effect of the working fluid along the path of the beam and not at just one point along the beam. For example, the raw data may be represented by a reduction in the voltage level output of a detector, which represents the beam intensity, as compared to the voltage level of the laser source that emitted the beam. The raw data may also be calibrated such that the detector output levels, e.g., voltage levels, correspond to conditions of the flow, such as flow velocity or mass.

The raw data 60 is populates the cells in the row 56 and column 58 of each of the data sets 50 and 52. The cells of raw data in row 56 and column 58 in each data set 50 and 52 are arranged to correspond to the spatial arrangement detectors in the array.

The data are arranged in a spatial array, such as a 2D array of cells 62 each corresponding to a row and column. The cells 62 of data exclude the raw data 60 of the detectors. The data in each cell 62 may represent the sum of the raw data 60 in the row 56 and column 58 corresponding to the cell 62. This approach of cell data representing sums detector outputs from a corresponding row and column is a conventional tomography approach to imaging a section of a physical system, such as a gas flow, by projecting penetrating waves, such as a laser beam, through the system.

The intensity and positioning information provides data from which 2D and 3D representations can be generated of the working fluid. These representations may be used to generate real time and dynamic presentations of the flow of the working fluid passing through or being exhausted from a gas turbine engine. The presentations may show in 2D and 3D, the velocity and direction of the flow, temperatures or temperature variations in the flow, distribution the composition of the flow, and other parameters regarding the flow.

The third data set 54 represents differences in the gas flow at a selected instant at which gas flows through plane P1 that is represented by data set 50 and the gas flows through plane P2 that is represented by data set 52. The third set 54 of data may be generated by comparing the data sets 50 and 52 from different planes P1 and P2 at a selected instance. Alternatively, the third data set 54 may be generated by comparing the data set in a single plane P1 at two or more instances. Each cell 64 in the third data set represents a difference between the corresponding cells in the other two data sets 50 and 52.

By providing information regarding the differences in the gas flow between two planes or two instances, the third data set 54 provides information on changes and variations in the gas flow over the distance (l) between the planes or the period between the instances of the data sets used to create the third data set. The third data set may be presented as a spreadsheet of data or a 2D or 3D image. The data in the cells 64 of the third data set may be collected over successive periods to provide information on the variation of the gas flow over time.

The third data set 54, as well as the other data sets 50, 52, may be used to evaluate the condition of the gas flow in the system, e.g. a gas turbine. The sets may be used to generate 2D and 3D images, or other information regarding the spatial distribution of the gas flow across a cross-section of the flow. For example, an image generated of either the first or second data sets 50 and 52 may have x and y axes, and third axis representing flow mass or velocity axis. A 3D image generated of the third data set 54 may have x and y axes and a third axis representing change of flow velocity between planes P1 and P2.

The distribution of gas flow may provide information regarding a particular can in the combustor, a worn or damaged bucket or nozzle in the turbine or other conditions of the gas turbine. The gas flow distribution information presented by the data sets may also be used to evaluate changes in flow as the engine speed changes, to optimize the position of the inlet guide vanes (IGV), adjust fuel flow to the combustor and monitor or adjust other engine operating parameters.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to collect data regarding a working fluid in a system comprising:
    arranging sources of beams proximate to a passage of the working fluid in or downstream of the system such that beams from the sources are projected through the working fluid, wherein the beams are arranged in planes traversing the working fluid, the planes are separated along an axis of the system, and the beams intersect at points within each of the planes;
    detecting intensities of the beams after they pass through the working fluid,
    using the detected intensities, determining data values representing a condition of the working fluid at positions in the planes corresponding to the intersections of the beams;
    comparing the data values associated with one of the planes to data values associated with another of the planes, and
    generating at least a two dimensional (2D) representation of the working fluid based on the comparison of the data values, wherein the at least 2D representation indicates changes in the working fluid as the working fluid flows between the planes.

2. The method of claim 1 wherein the beam sources comprise sources of laser beams.

3. The method of claim 1 wherein the planes are perpendicular to the axis of the system.

4. The method of claim 1 wherein the planes are separated by one to ten millimeters.

5. The method of claim 1 wherein the beam sources are arranged in rows and a columns orthogonal to the rows.

6. The method of claim 1 wherein the system is at least one of a turbo-machine, steam turbine and a gas turbine, and the beam sources are arranged to project the beams through an exhaust gas portion of the working fluid.

7. The method of claim 1 wherein the generation of the at least 2D representation of the working fluid includes applying optical tomography to generate the representation of the working fluid.

8. The method of claim 1 further comprising generating determining differences between successive planar arrays of the beam sources and using the differences to generate the at least 2D representation.

9. A method to collect and present data regarding a working fluid in a gas turbine comprising:
   arranging laser beam sources proximate to a passage of a working gas in or downstream of the gas turbine such that laser beams from the sources are projected through the working gas, wherein the laser beam sources are arranged such that the paths of the beams are distributed in planes each including a cross-sectional planar area of the working gas and each path intersects with at least one other of the paths;
   detecting intensities of the beams after passing through the working gas;
   determining for each plane, data values each corresponding to an intersection of the paths, wherein each of the data values is determined by the detected intensities of the beams passing through the corresponding intersection;
   comparing the data values in the planes, and
   generating at least a two dimensional (2D) representation of the working gas based on the comparison of the data values in the planes, wherein the 2D representation illustrates changes in the working gas as the gas moves between the planes.

10. The method of claim 9 wherein the laser beam sources and the beams are arranged in a plane perpendicular to an axis of the gas turbine.

11. The method of claim 9 wherein the laser beam sources and the beams are arranged in planes perpendicular to a rotational axis of the gas turbine.

12. The method of claim 9 wherein the laser beam sources are arranged in rows and columns orthogonal to the rows.

13. The method of claim 9 wherein the generation of the at least 2D representation of the working gas includes applying optical tomography analysis to generate the 2D representation.

14. An apparatus to analyze a working fluid passing through a turbo-machine comprising:
   a first array of laser sources and detectors arranged in a first plane a plane extending through the working fluid as the fluid passes through or downstream of the turbo-machine, wherein the laser sources of the first array are arranged to project laser beams intersecting beams projected by other ones of the laser sources of the first array;
   a second array of laser sources and detectors arranged in a second plane extending through the working fluid as the fluid passes through or downstream of the turbo-machine, wherein the laser sources of the second array are arranged to project laser beams intersecting beams projected by other ones of the laser sources of the second array and wherein the second array is parallel to and offset from the first array along a rotational axis of the turbo-machine, and
   a controller receiving laser intensity data from the detectors and including a non-transitory memory storing instructions and a processor which executes the instructions to cause the controller to determine data values each corresponding measurements by the detectors of the intersecting beams emitted by the laser sources, and generating a representation of changes in the working gas as the working gas flows between the first and second array based on comparisons the data values of the working gases at the intersections of the beams and in the first and second arrays.

15. The apparatus of claim 14 wherein the laser sources and detectors in each of the first array and second array are arranged in rows and columns orthogonal to the rows.

16. The apparatus of claim 14 wherein the turbo-machine is a gas turbine.

* * * * *